United States Patent [19]

Hnatowich

[11] Patent Number: 4,479,930

[45] Date of Patent: Oct. 30, 1984

[54] AMINES COUPLED WTH DICYCLIC DIANHYDRIDES CAPABLE OF BEING RADIOLABELED PRODUCT

[75] Inventor: Donald J. Hnatowich, Worcester, Mass.

[73] Assignee: Trustees of the University of Massachusetts, Amherst, Mass.

[21] Appl. No.: 401,834

[22] Filed: Jul. 26, 1982

[51] Int. Cl.$^3$ .................. A61K 43/00; A61K 49/00
[52] U.S. Cl. ............................ 424/1.1; 260/429 J; 424/9
[58] Field of Search ............... 424/1.1, 9; 260/429 J

[56] References Cited

U.S. PATENT DOCUMENTS 4,385,046 5/1983 Milbradt et al. .................. 424/1

FOREIGN PATENT DOCUMENTS 0035765 9/1981 European Pat. Off. ............ 424/1.1
0038546 10/1981 European Pat. Off. ............ 424/1.1
2067203 7/1981 United Kingdom ................ 424/1.1

OTHER PUBLICATIONS

Hnatowich et al., Int. J. Appl. Radiat. Isot., 33:327–332 (1982).

Primary Examiner—Christine M. Nucker
Attorney, Agent, or Firm—Paul J. Cook; Lawrence Gilbert

[57] ABSTRACT

A dicyclic dianhydride rapidly and efficiently couples with a broad variety of amines such as polypeptides and proteins in non-aqueous or aqueous media and then may be chelated with a wide choice of radioisotope metallic cations to yield a radio-labeled product that is stable in vivo. A simple 1-step synthesis of the coupled amine in aqueous solution of neutral pH is described which requires only a few minutes time and with little accompanying hydrolysis.

18 Claims, 4 Drawing Figures

AMINES COUPLED WITH DICYCLIC DIANHYDRIDES CAPABLE OF BEING RADIOLABELED PRODUCT

FIELD OF THE INVENTION

This invention relates to amines coupled with a dicyclic dianhydride and which are capable of being chelated with a metal radionuclide and to the radiolabeled compositions produced by chelation.

BACKGROUND OF THE INVENTION

Prior to the present invention, proteins such as antibodies have been radiolabeled with iodine. A more attractive approach to the radiolabeling of amines, polypeptide chains and proteins has been the "bifunctional chelate" methods in which a strong chelating group is covalently bonded to the protein which, in turn, is labeled with a variety of chelatable radionuclides. In the resultant product, the protein retains its biological function and the product also retains the radionuclide. When the chelating group chosen forms stable chelates, the radiolabel is likely to be stable in vivo. In addition, its presence will have only a minor effect on the specificity or other functional biochemical characteristics of the protein.

Attempts have been made to develop useful bifunctional chelates. Sundberg et al [*J. Med. Chem.*, 17:1304 (1974)] was concerned with synthesizing 1-(p-benzyldiazonium)-EDTA as a chelating agent. Their method ultimately provided a labeled protein but the 7-step synthesis of the EDTA (ethylenediaminetetraacetic acid) intermediate makes this approach very unattractive. Yeh et al [*J. Radioanalytical Chem.*, 53:327 (1979)] developed a method using 1-(p-carboxymethoxybenzyl)-EDTA as the linking molecule but without avoiding similar disadvantages. Others [Krejcarek et al, *Biochem. Biophys. Res. Comm.*, 77:581 (1977); and Wagner et al, *J. Nucl. Med.*, 20:428 (1979)] developed a method of linking diethylenetriaminepentaacetic acid (DTPA) to proteins via the synthesis of a mixed carboxycarbonic anhydride intermediate. The synthesis of this intermediate, although less complicated than others, is nevertheless not simple; the coupling reaction alone requires about 12 hours duration and must be followed by several purification steps requiring several days' time. Gluteraldehyde has also been considered as a method of coupling chelating agents to proteins [Pritchard et al, *Proc. C. Soc. Exp. Biol. Med.*, 151:297 (176); Yokoyama et al, *J. Nucl. Med.*, 22:32 (1981)], but the formation of dimers and the need to reduce the product in order to improve its stability in vivo are major disadvantages.

Overall, therefore, there is a long demonstrated need for a simple and efficient bifunctional chelating agent for amines, polypeptides and proteins and other medically important compounds such that their radiolabeled forms are stable in vivo and retain their specific biological activities to a substantial degree.

SUMMARY OF THE INVENTION

The compositions of this invention are prepared by reacting an amine with a dicyclic dianhydride of the formula

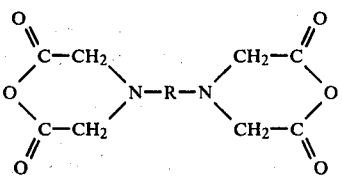

wherein R is a linking group containing from 1 to 25 carbon atoms and which can include nitrogen atoms and/or carboxyl groups or other groups which do not denature proteins or peptides and which do not interfere with the hydrolyzed decyclic dianhydride ability to chelate metal ions. The compositions of this invention also include the radiolabeled reactive product of the amine with the dicyclic dianhydride.

DETAILED DESCRIPTION OF THE EMBODIMENTS

Figure 1:
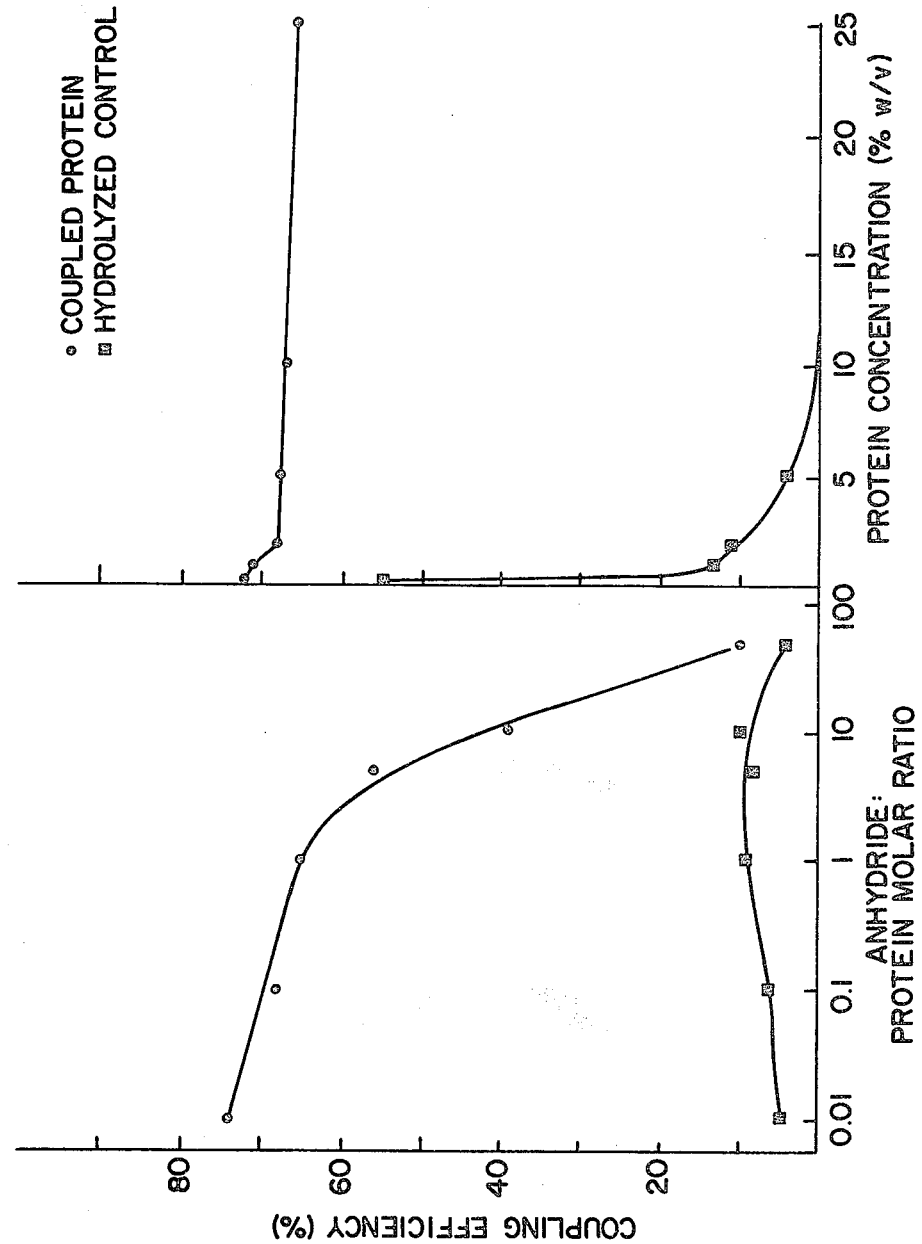
FIG. 1 shows the variation of the coupling efficiency with the composition of the reaction.

In its broadest aspect, the invention is a novel method of radiolabeling for the localization and detection of amines, polypeptides and proteins. The invention comprises three parts: a radioactive metal isotope—a radionuclide; a chelating agent of the formula $R(N(CH_2CO)_2O)_2$ wherein R is defined above; and a primary or secondary amine. In order to obtain a full and clear comprehension of the many possible embodiments within the scope of the present invention, each of these requisite components will be described individually.

Radionuclide

One of the advantages of the present invention is that, in principle, virtually any metal radionuclide may be used as a label. The preferred metal radioisotopes for use because of their ready availability are gallium-67 (hereinafter $^{67}Ga$) having a half-life of 2.6 days, Indium-111 (hereinafter $^{111}In$) having a half-life of 2.8 days, and because of its nearly ideal properties for imaging, Technetium-99m (hereinafter $^{99m}Tc$) having a half-life of only 6 hours. The sources of such metallic catonic radioisotopes are well known in the art and need not be described in detail here.

Chelating Agents

Those compositions suitable as chelating agents when hydrolyzed are represented generally by the structure

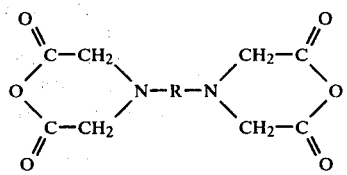

wherein R is defined above and is preferably $CH_2CH_2N(CH_2COOH)CH_2CH_2$ or ethylene. The preferred chelating agents are hydrolyzed forms of the cyclic dianhydrides of ethylenediaminetetraacetic acid (hereinafter EDTA) and diethylenetriaminepentaacetic acid (hereinafter DTPA).

Chelating agents having the general structural formula represented above are, in their cyclic anhydride forms, efficient coupling agents able to couple to many different amines, such as polypeptides or proteins. Coupling efficiency is defined herein as that number of dicyclic dianhydride molecules which form amide bonds with the amine divided by the total number of cyclic dianhydride molecules added initially. It is apparent that R in the general formula will include many simple and complex combinations of carbon, hydrogen, nitrogen and other atoms. Accordingly, all chelating agents having the general formula given above and having a coupling efficiency greater than 1% are deemed to be within the scope of this invention.

Amines, Polypeptides and Proteins

An almost infinite variety of primary or secondary amines in non-aqueous and aqueous media will be bound by the dicyclic dianhydride chelating agents described herein. Examples of suitable primary or secondary amines are those polypeptide chains and proteins having immunological functions such as antibodies and fragments of antibodies such as F(ab) and F(ab')$_2$ fragments, all of which form stable amides with the dicyclic dianhydride which amides are capable of chelating a metal radionucleotide. Other compounds of interest such as plasma proteins, typically albumins and fibrinogen, also form stable amides.

In view of the broad and varied class of compounds which may be bound by these chelating agents and then chelated to a radionuclide to form a stable radiolabeled product in vivo, all chemical compositions having at least one amine group available for binding as an amide bond with these anhydrides are deemed to be within the scope of the present invention.

For purposes of illustrative clarity and ease of comprehension, only one of the preferred chelating agents—the dicyclic dianhydride of DTPA—will be referred to hereinafter. It shall be understood, however, that the use of this particular chelating agent for descriptive purposes shall not restrict nor limit the use or applicability of other chelating agents having the general structure described earlier. It is to be recognized, however, that other chelating agents similar to DTPA and having the requisite cyclic dianhydride structure may be less efficient as chelating agents than DTPA.

The dicyclic dianhydride of DTPA can be prepared according to the method of Eckelman et al [*C. J. Phrm. Sci.*, 64:704 (1975)]. Typically, 0.1 mol of the acid is heated with a 4-fold molar excess of acetic anhydride in 50 milliliter (hereinafter ml) of pyridine at 65° C. for 24 hours. The resulting anhydride is insoluble in the reaction mixture and is collected by filtration, purified by repeated washing with acetic anhydride and subsequently with anhydrous ether. Drying in an oven at 50°-60° C. removes the last traces of solvent.

To minimize hydrolysis during coupling, the prepared dicyclic dianhydride added as a solid to the primary or secondary amine of interest or a solution of the amine can be added to the solid dicyclic dianhydride followed by rapid solubilization of both reactants in 0.1 M Hepes buffer or phosphate buffered saline (hereinafter PBS) at pH 7.0. Typically, 20 microliters (hereinafter μl) containing 0.4 milligrams (hereinafter mg) of antibody protein buffered at pH 7.0 with Hepes buffer or PBS is added to approximately 0.7-0.9 μg of solid cyclic dianhydride and the solution agitated for 1 minute. In cases where the amount of dianhydride is too small to be conveniently weighed, a 0.1 mg per ml suspension of the dianhydride in chloroform is prepared and aliquots containing the described mass added to the reaction with subsequent evaporation to dryness at room temperature by a flow of nitrogen. No detectable increase in coupling efficiency is observed in those cases where the reaction was allowed to proceed longer than 1 minute or even in those instances where the reaction was continued over night. The initial and final pH of the reaction mixture is pH 7.0 in all instances. Coupling efficiencies, defined as the percentage of anhydride molecules which covalently attach to the polypeptide or protein, is high when anhydride to antibody molar ratios are held at 1:1. The efficiency of coupling decreases at pH values above or below neutrality, with decreasing molar ratios and with decreasing concentrations of protein. The conjugated protein is separated and purified from free DTPA either by dialysis at 40° C. or by a single passage through a Sephadex G-50 gel filtration column.

Radioisotope labeling by ligand exchange is accomplished by adding a 0.05 M acetic solution of the selected radionuclide to the protein solution either before or after purification from the residual free DTPA cyclic dianhydride. It is preferred that the radionuclide labeling be done after purification and elimination of the free DTPA as this avoids excess handling with radioactive materials. A suitable radionuclide is $^{111}$In as the acetate which can be prepared by adding equal volumes of 0.1 M sodium acetate to a $^{111}$In chloride solution such that a pH of 5.5-6.0 and an acetate concentration of 0.05 M is obtained. Following the addition of $^{111}$In acetate in 0.05 M acetate buffer to the conjugated protein solution, transcomplexation occurs quantitatively under normal circumstances.

For purposes of empirically evaluating the examples described below, hydrolyzed control experiments were conducted in which the deliberate hydrolysis of the dicyclic dianhydride of DTPA prior to adding the protein solution was the only change in the procedure. Such hydrolyzed control experiments are useful to determine whether radionuclides will bind to chelated proteins selectively or will bind non-specifically to the test compositions. In the examples described below, the hydrolyzed control studies resulted in no detectable radioactivity being bound to the protein under normal circumstances. Hydrolyzed control experiments were performed by adding 1.0 ml of the Hepes buffer to the mass of solid anhydride and allowing hydrolysis to proceed either at room temperature for 60 minutes or briefly heating the solution to boiling. The protein was then added and the study thereafter conducted in identical manner for all samples.

As evidenced by the studies described hereinafter, the present invention provides unique and valuable advantages not previously available with prior art methodologies employing radioisotopes as a label: First, the coupled amine may be purified from the hydrolysis products before addition of any radioactivity, thereby avoiding the need to handle radioactive samples during the purification process. Second, the coupling with the dicyclic dianhydride of DTPA is efficient and simple after which the coupled product maintains its ability to bind a radioactive label subsequently for a long period of time of at least a month. Such coupled and purified protein solutions may be stored in buffer at 4° C. without detectable or deleterious effects for at least several weeks and then radiolabeled only when required. Third, labeling with the radionuclide, depending as it does on the chetation process, is often extremely rapid and is, in the case of [111]IN, completed upon mixing of the radioisotope and coupled protein solution. Other advantages include the choice of a large variety of metallic radionuclides, having different imaging and detection properties, radiation properties and half-lives —all of which should form strong chelates with DTPA-coupled primary and secondary amines, e.g. polypeptides and proteins. Finally, the dicyclic dianhydride coupling method described herein is a most simple and time efficient alternative to radioiodination of proteins and other amine-containing compounds.

The following examples are merely illustrative of the present invention and are not intended to limit or restrict the invention in form or scope.

EXAMPLE I

The cyclic dianhydride of DTPA was added to solid human serum albumin (essentially globulin free) and followed by rapid solubilization of both compounds in 1.0 ml of 0.1 M Hepes buffer at pH 7.0. The coupling reaction was allowed to proceed at room temperature with agitation for 1 minute prior to radiolabeling. As earlier described, no detectable increase in coupling efficiency was observed in those samples where the reaction was allowed to proceed overnight and the initial and final pH of the reaction mixture remained at pH 7.0. Radio-labeling was accomplished by adding 0.05 M acetate solution of $^{111}$In to the albumin solution either before or after purification from residual free DTPA. The [111]IN solution was prepared by adding an equal volume of 0.1 M sodium acetate to the [111]IN chloride solution so that the final pH was 5.5–6.0 and the final acetate concentration was 0.05 M.

The method used to measure coupling efficiency was exhaustive dialysis at room temperature against 1 liter of distilled water. Initially, the coupled albumin and corresponding hydrolyzed controls were purified from residual free DTPA by dialysis for 2 days before the addition of the [111]IN label, followed by dialysis for an additional 2 days. Under these conditions, 59±2% and 35±5% of the activity remained in the dialysis bag for the coupled albumin and the hydrolyzed control sample respectively. Subsequently, relative coupling efficiency was extimated by the dialysis of protein samples which were not predialyzed before radiolabeling. Under these conditions, only 7±3% of the activity remained in the hydrolyzed control samples after 2 days of dialysis, the activity remaining in the corresponding coupled albumin samples was a minimum of approximately 75%. Dialysis without prepurification of the protein became the method of choice in measuring relative coupling efficiencies to demonstrate the effects of variances in molar ratios and protein concentration.

As may be seen in FIG. 1, the coupling efficiency using a fixed albumin concentration of 18.8 mg per ml is a function of the anhydride to protein molar ratio (molecular weight of anhydride 357, molecular weight of protein 67,000). Although the number of chelating groups coupled to each albumin molecule increases with increasing molar ratio, the coupling efficiency decreases. Furthermore, the effect of increasing protein concentration at a fixed anhydride to protein molar ratio of 0.1:1 is shown on the right in FIG. 1. It is apparent that a decreased coupling efficiency is obtained with each increase in protein concentration.

Protein coupling and labeling may be performed using a variety of buffers. Different solutions of 0.1 M borate buffer (pH 8.0), phosphate buffer (pH 7.0) and acetate buffer (pH 6.0) can be used in place of Hepes buffer. After coupling at a 1:1 molar ratio using a protein concentration of 18.8 mg/ml and labeling with [111]IN acetate solution, and dialysis for two days, the activities were as follows: 42% for borate buffer (control 4%); 45% for phosphate buffer (control 12%); and 37% for acetate buffer (control 7%).

Figure 2:
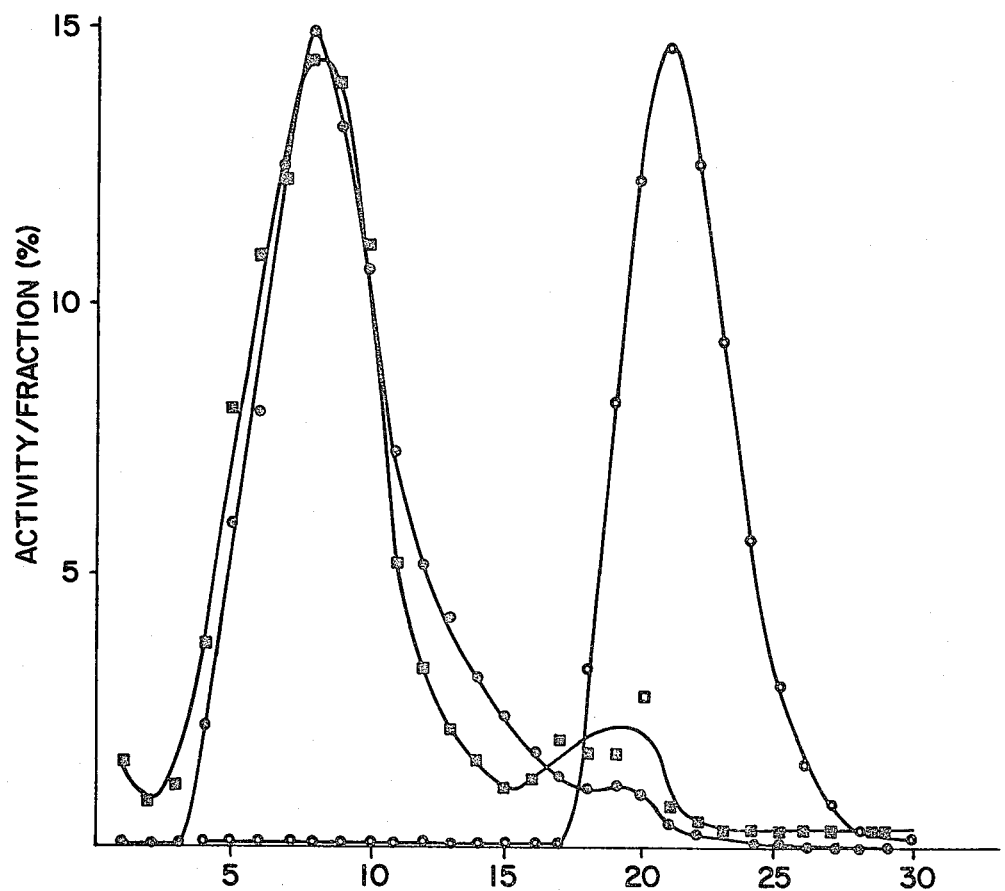
FIG. 2 shows the chromatographic results of radiolabeled albumin.

To determine whether the coupled protein may be separated from residual free DTPA via passage through a gel filtration column, a DTPA chelated albumin preparation coupled at a 1:1 molar ratio was passed through a 1.0×20 cm column Sephadex G-50. The fractions containing the protein were collected, labeled with [111]IN as previously described and analyzed by Sephadex G-50 chromatography. The results are as indicated in FIG. 2. The activity eluted completely in one peak containing the protein (centered at fractions 8–9 of FIG. 2). Under identical conditions, non-specifically bound [111]IN activity in the hydrolyzed controls elutes only partially and in two distinct peaks.

Finally, biodistributions of the radiolabeled chelated albumin were conducted in relation to $^{125}$I-albumin prepared conventionally. Biodistributions at 45 minutes were determined in normal CD-1 male mice with the results as shown in Table I below.

TABLE I

|  | Unpurified $^{111}$In-albumin | [111]In hydrolyzed control | Purified $^{111}$In-albumin | [125]In-albumin |
|---|---|---|---|---|
| Liver | 3.82(0.40) | 0.49(0.11) | 3.48(9.02) | 3.58(0.26) |
| Heart | 4.04(0.22) | 0.21(0.13) | 4.30(0.33) | 4.36(0.15) |
| Lungs | 5.56(0.95) | 0.35(0.11) | 6.56(0.12) | 7.68(0.93) |
| Kidney | 14.6(0.60) | 3.53(1.82) | 6.24(0.88) | 3.80(0.45) |
| Spleen | 3.46(0.40) | 1.15(0.45) | 3.64(0.47) | 4.15(0.31) |
| Brain | 0.52(0.09) | 0.09(0.06) | 0.50(0.04) | 0.63(0.15) |
| Muscle | 0.56(0.08) | 0.28(0.21) | 1.26(0.09) | 0.83(0.11) |
| Bone | 2.97(0.48) | 0.67(0.33) | 3.72(0.26) | 2.80(0.29) |
| Blood | 30.6(3.20) | 0.60(0.26) | 32.8(1.30) | 35.4(3.10) |
| Activity recovered (%) | 90% | 7% | 102% | 102% |

*% Injected dose/g normalized to 25 g mouse with one SD of the mean in parenthesis (N = 6)

Biodistributions were determined for a coupled preparation having a protein concentration of 18.8 mg/ml albumin and coupled at a molar ratio of 1:1 with DTPA cyclic dianhydride dialyzed for two days and then labeled with [111]IN as previously described herein. For comparison, biodistributions were also obtained for commercially available $^{125}$I-albumin. In order to determine the biodistribution of the hydrolyzed controls, a hydrolyzed preparation of albumin was prepared with [111]IN and dialyzed for a single day so that enough activity would remain in the hydrolyzed sample for the animal study. For comparison, a purified albumin preparation, coupled as described herein, was labeled and also dialyzed for a single day. In this latter preparation, further dialysis of an aliquot showed that the injectate contained about 10% free activity. In all preparations, the injectate for the test mice consisted of 0.2 ml containing approximately 2% albumin and 1–10 μCi of [111]IN or $^{125}$I activity.

A comparison of the results shown within Table I of the four biodistribution studies reveals that the purified $^{111}$IN-labeled albumin is distributed in a nearly identical manner to that of radioiodinated albumin. The values for the unpurified $^{111}$IN-albumin show a lower blood and higher kidney accumulation than either the purified $^{111}$IN-albumin or iodinated albumin reflecting the 10% free activity in this sample. However, values for the hydrolyzed controls are vastly different from the other test samples in each tissue type.

EXAMPLE II

Fibrinogen Coupled to $^{111}$IN-DTPA.

Fibrinogen coupled DTPA was prepared as previously described herein and the coupled fibrinogen preparations were purified before radiolabeling by a single passage through a Sephadex G-50 column and a column of Sepharose 6B at room temperature using 0.05 M Hepes buffer, 0.9% sodium chloride, and buffer eluant. Labeling was accomplished by adding a 0.05 M acetate solution of $^{111}$IN to the reaction solution. Fractions were collected and the concentration of protein in each determined by measuring absorption at 280 nanometers with respect to a known standard. The most absorbent fractions were collected.

To determine whether fibrinogen retains its biochemical functional ability after radiolabeling by this method, an in vivo clotting assay was performed in which clotting time was determined at three stages of preparation and labeling after formation of the DTPA chelate. The results are presented in Table II and demonstrate that the clotting time for coupled human fibrinogen and its hydrolyzed control were in good agreement at each stage of the preparation.

TABLE II

|  | Clotting Time (sec) | |
| --- | --- | --- |
| Stage of Preparation | Coupled protein | Hydrolyzed Control |
| Following coupling | 43(43–44) | 39(37–40) |
| Following G-50 purification | 38(35–40) | 39(38–39) |
| Following labeling and dialysis | 24(23–25) | 27(25–29) |

The stability of coupled human fibrinogen in plasma and serum environments was evaluated using a 0.5 ml aliquot of the labeled preparation which contained 10 mg of fibrinogen and 2.0 ml of human plasma at 37° C. The final concentration of DTPA was approximately 100 micromolar ($\mu$M). Following incubation for 24 hours, aliquots of untreated and $^{111}$IN-labeled fibrinogen dilutions stored in saline were analyzed by Sepharose 6B chromatography. Analysis in the same chromatographic system confirmed that plasma transferrin therein was capable of binding additional $^{111}$IN. There was no increase in $^{111}$IN-DTPA in the incubated sample showing that no appreciable hydrolysis of the amide bond had occurred. Similarly, there was no evidence of a new $^{111}$IN peak transferrin in the results indicating that no appreciable dissociation of the chelate had occurred.

Figure 3:
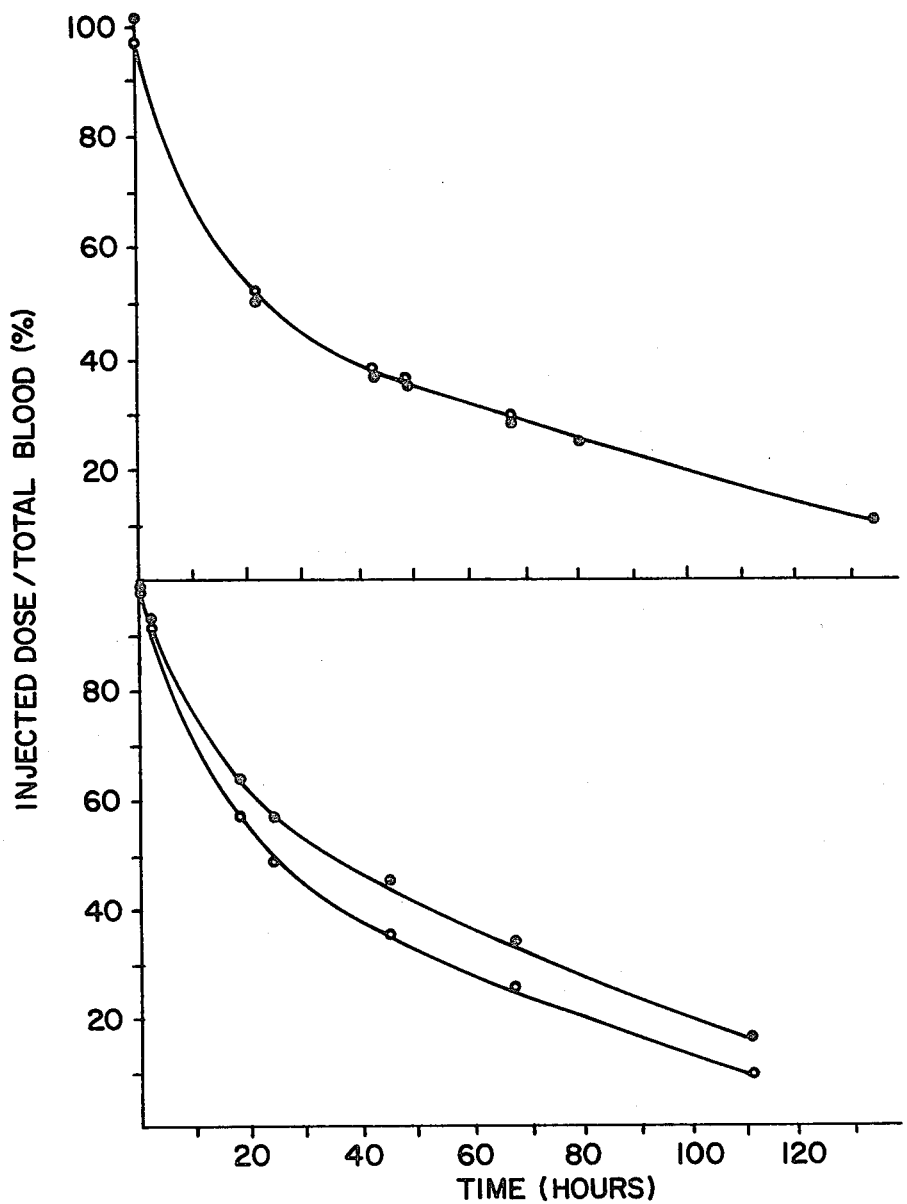
FIG. 3 shows the rate of blood clearance of the composition of this invention.

Blood clearance and in vivo clottability studies were performed using normal mongrel dogs which had not previously received human fibrinogen. Both 1:1 and 5:1 molar ratio coupled protein samples were prepared, purified and radiolabeled with $^{111}$IN. These preparations had specific activities of 1 $\mu$Ci/mg and 2 $\mu$Ci/mg respectively. Each preparation was divided for use in measuring blood clearance and in vivo clottability. Blood clearance was measured following administration of the $^{111}$IN samples to 2-3 dogs along with commercially obtained $^{125}$I-human fibrinogen in such dosages that each animal received approximately 100 $\mu$Ci of $^{111}$IN and 20 $\mu$Ci of $^{125}$I-labeled fibrinogen. The animals were injected in a peripheral vein and blood samples were removed from the collateral vein. The results, as presented in FIG. 3, show that in the case of the 1:1 and 1:5 molar ratio coupled protein, the rates of clearance for the 2 labels were essentially identical. Equally important, the range of values in all $^{111}$IN labeled preparations is within the $^{125}$I-fribrinogen range of determinations.

EXAMPLE III

Coupling to Polyclonal, Monoclonal Antibody and IgG Fragments

Coupling to antibody and antibody fragments was accomplished as previously described for albumin and fibrinogen. A solution of the antibody of interest, typically 20 ml of a solution containing 0.4 mg of protein and buffered at pH 7.0 with 0.05 M Hepes or PBS, was added to the solid cyclic dianhydride of DTPA in 0.7–0.9 $\mu$g quantities and the solution agitated for 1 minute.

Investigation of polyclonal antibodies and monoclonal antibodies yielded the following observations held in common by all these immunological active proteins. The coupling efficiency is 40±5% when anhydride to antibody molar ratios of 1:1 are used. Efficiency of coupling decreases at pH values above and below pH 7.0. The efficiency of coupling decreases with increasing molar ratios of anhydride to antibody and with decreasing protein concentrations. The coupled antibody is purified from free residual DTPA either by dialysis at 4° C. or by a single passage through a Sephadex G-50 gel filtration column similar to that shown for albumin and fibrinogen. Following the addition of a $^{111}$In in approximately 0.05 M acetate buffer, transcomplexation occurs essentially quantitatively and the final radiolabeled product is stable for a long time period.

Figure 4:
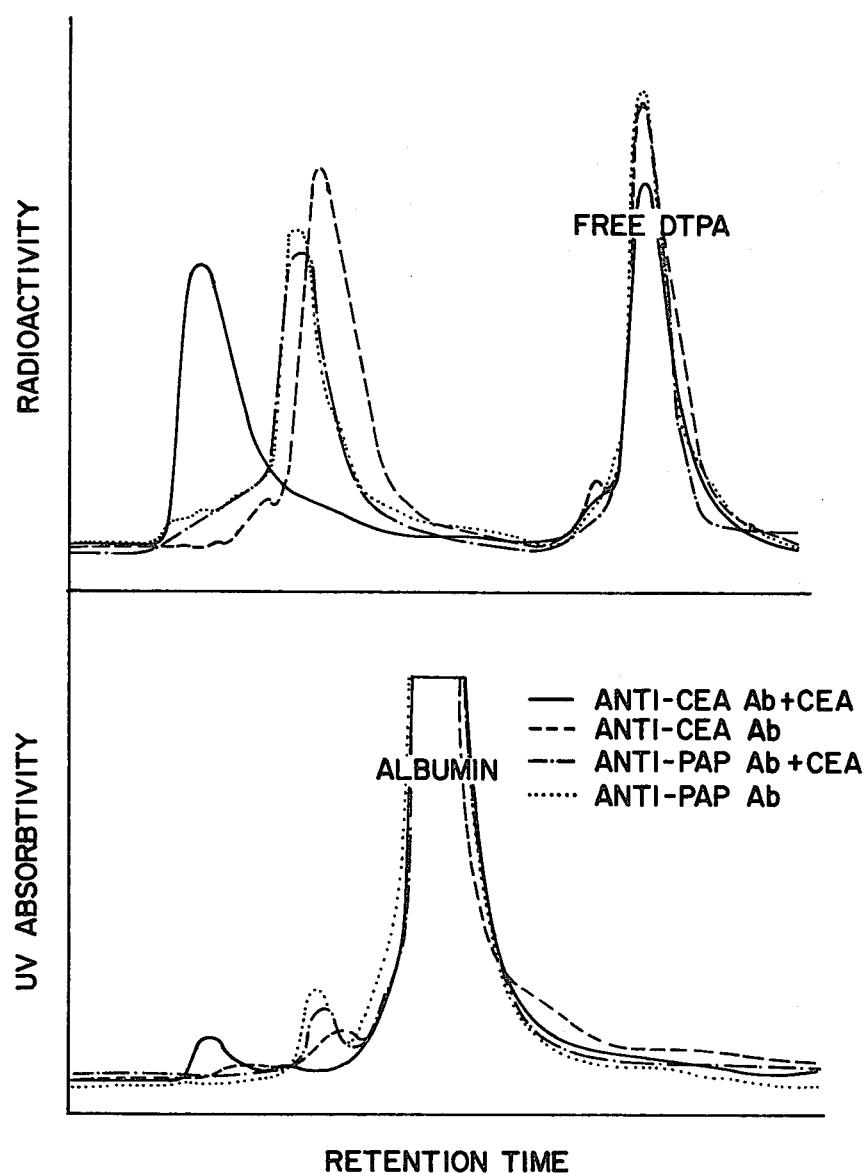
FIG. 4 shows the column retention of labeled anti-CEA and anti-PAP.

The ability of labeled radionuclide chelated antibody to bind its antigen has been investigated under in vitro and in vivo conditions using monoclonal anti-carcinoembryonic antigen (hereinafter anti-CEA) antibody and, as a control, monoclonal anti-prostatic acid phosphatase (hereinafter anti-PAP) antibody. By affinity chromatography, an average of 92% of the labeled anti-CEA antibody was retained by column CEA while the control anti-PAP antibody showed only 6% retention. Antibody integrity was also evaluated using high performance liquid chromatography separation of the labeled proteins before and after the addition of CEA. As is shown in FIG. 4, the retention time of the control anti-PAP antibody peak, as detected by radioactivity and UV absorptivity, remains unchanged by the addition of its specific antigen, while a shift towards a shorter retention time is apparent in the case of the anti-CEA antibody; this is due to the binding of the anti-CEA antibody with its specific antigen. The shift is essentially quantitative, indicating again that the radiolabeling of the anti-CEA antibody does not noticeably affect its ability to bind to its specific antigen.

Biodistributions of $^{111}$IN-labeled anti-CEA antibody and control anti-PAP antibody were performed in male BALB-C nude mice possessing human colorectal cancer xenographs either in the left subrenal capsule or in the left ear. This tumor was originally derived from the HT-29 cell line which is known to secrete CEA. The tumors in the animals were used after 15 to 18 days post-implantation. Each animal was administered by vena puncture a dosage of 0.1 ml (with subrenal implants) or 0.2 ml (with ear implants) containing 100 μg/ml of $^{111}$IN-labeled anti-CEA antibody or $^{111}$IN-labeled anti-PAP antibody in 10% bovine serum albumin and isotonic 0.05 M Hepes buffer. These antibodies had specific activities of 0.1-3.0 μCi/μg. The subrenal implanted animals were sacrificed at 24 hours post-injection while the intrapinnal (ear implant) animals were first imaged serially and then sacrificed at 72 hours post-injection time. Biodistribution results are presented in Table III and expressed as the percent of the injected dose per gram of tissue (wet weight of tissue normalized to a 25 gram animal). As shown therein, the accumulation of labeled anti-CEA antibody in tumor tissue was 4 times greater than that of the control anti-PAP antibody and the tumor to blood ratio was 5.2 for the anti-CEA antibody versus 1.2 for the control anti-PAP antibody. A subsequent repetition of this study showed that the accumulation in tumor tissue for the labeled anti-CEA antibody rose to 40.5% while the anti-PAP control accumulation within the tumor remained at 8.3%. Another study, identical in all respects except that the antibodies were radioiodinated with $^{125}$I, showed that the accumulation of radiolabeled antibody in the tumor was found to be 19.4% for the anti-CEA antibody and 4.0% for the anti-PAP antibody, with tumor to blood ratios of 1.8 and 0.6 respectively. Biodistribution results for the intrapinnal implanted animals also showed increased accumulation in tumor tissue for the $^{111}$IN-labeled anti-CEA antibody at 20.6% per gram, whereas the control anti-PAP antibody showed only a 2.71% per gram accumulation. In the intrapinnal implant tumor, the labeled anti-CEA to labeled anti-PAP antibody ratio is approximately 8 as compared to a ratio of about 4 in the subrenal implanted animal studies.

TABLE III

|  | Anti-CEA (N = 6) | Anti-PAP (N = 6) |
|---|---|---|
| Brain | 0.25 ± 0.06 | 0.26 ± 0.14 |
| Heart | 2.09 ± 0.05 | 2.42 ± 0.79 |
| Lung | 3.84 ± 1.25 | 4.15 ± 1.92 |
| Liver | 5.52 ± 1.77 | 1.65 ± 2.51 |
| Spleen | 3.94 ± 0.85 | 10.90 ± 4.10 |
| Rt. Kidney | 9.25 ± 2.85 | 7.61 ± 2.49 |
| Lt. Kidney | 7.91 ± 1.51 | 7.34 ± 2.29 |
| Tumor | 37.90 ± 11.80 | 9.47 ± 0.24 |
| Muscle | 0.59 ± 0.15 | 0.53 ± 0.24 |
| Blood | 7.30 ± 0.92 | 7.19 ± 4.17 |

What we claim is:

1. A chemical composition comprising:
   a primary or secondary amine comprising at least one amine group available for bonding as an amide bond;
   a radioactive metallic cation; and
   a chelating agent derived from a compound of the formula

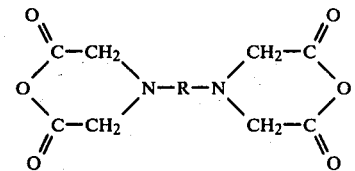

wherein R is a linking moiety containing between 1 and 25 carbon atoms, said chelating agent being bound to said amine group and to said metallic cation.

2. A chemical composition of claim 1 wherein said chelating agent is the dicyclic dianhydride of diethylenetriaminepentaacetic acid.

3. A chemical composition of claim 1 wherein said chelating agent is the dicyclic dianhydride of ethylenediaminetetraacetic acid.

4. The composition of claim 1, 2 or 3 wherein the radioactive metallic cation is selected from the group consisting of gallium-67, indium-111 and technetium-99m.

5. The composition of claim 1, 2 or 3 wherein the amine comprises a polypeptide chain.

6. The composition of claim 1, 2 or 3 wherein the amine comprises a protein.

7. A process for making a radionuclide labeled composition comprising the steps of:
   preparing a solid chelating agent having the formula

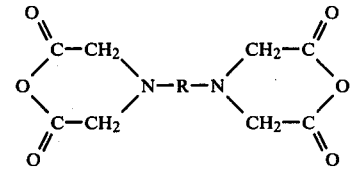

wherein R is a linking moiety containing between 1 and 25 carbon atoms;
   mixing said solid chelating agent with a primary or secondary amine containing at least one amine group able to form an amide bond with said chelating agent; and
   adding a radioactive metallic cation to said conjugate to form a transcomplexed molecule.

8. The method as recited in claim 7 wherein said chelating agent is selected from the group consisting of the dicyclic dianhydride of diethylenetriaminepentaacetic acid and the dicyclic dianhydride of ethylenediaminetetraacetic acid.

9. The method as recited in claim 7 wherein said amine is selected from the group consisting of a polypeptide and a protein.

10. The method as recited in claim 7 wherein said radioactive metallic cation is selected from the group consisting of gallium-67, indium-111 and technetium-99m.

11. A chemical composition comprising:
   a primary or secondary amine comprising at least one amine group available for bonding as an amide bond; and
   a chelating agent derived from a compound of the formula

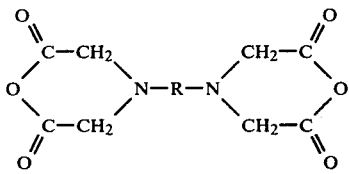

wherein R is a linking moiety containing between 1 and 25 carbon atoms, said chelating agent being bound to said amine group and to said metallic cation.

12. A chemical composition of claim 11 wherein said chelating agent is the dicyclic dianhydride of diethylenetriaminepentaacetic acid.

13. A chemical composition of claim 11 wherein said chelating agent is the dicyclic dianhydride of ethylenediaminetetraacetic acid.

14. The composition as recited in claim 1, 2 or 3 wherein the amine comprises a polypeptide chain.

15. The composition as recited in claim 1, 2 or 3 wherein the amine comprises a protein.

16. A process for making a radionuclide composition capable of chelating metal comprising the steps of: preparing a solid chelating agent derived from a compound having the formula

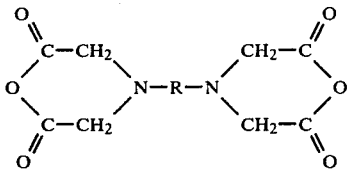

wherein R is a linking moiety containing between 1 and 25 carbon atoms; and mixing said solid chelating agent with a primary or secondary amine containing at least one amine group able to form an amide bond with said chelating agent.

17. The method as recited in claim 16 wherein said chelating agent is selected from the group consisting of the dicyclic dianhydride of diethylenetriaminepentaacetic acid and the dicyclic dianhydride of ethylenediaminetetraacetic acid.

18. The method as recited in claim 16 wherein said amine is selected form the group consisting of a polypeptide and a protein.

* * * * *